(12) United States Patent
Kane et al.

(10) Patent No.: US 9,655,910 B2
(45) Date of Patent: May 23, 2017

(54) COMPOSITIONS AND METHODS FOR TREATING ADDICTION

(71) Applicants: Edward Kane, Millville, NJ (US); Patricia Kane, Millville, NJ (US); Brett T Hauser, Millville, NJ (US)

(72) Inventors: Edward Kane, Millville, NJ (US); Patricia Kane, Millville, NJ (US); Brett T Hauser, Millville, NJ (US)

(73) Assignee: BODYBIO INC., Millville, NJ (US)

( * ) Notice: Subject to any disclaimer, the term of this patent is extended or adjusted under 35 U.S.C. 154(b) by 0 days.

(21) Appl. No.: 14/634,876

(22) Filed: Mar. 1, 2015

(65) Prior Publication Data

US 2015/0265636 A1    Sep. 24, 2015

Related U.S. Application Data

(60) Provisional application No. 61/969,066, filed on Mar. 21, 2014.

(51) Int. Cl.
*A61K 31/05* (2006.01)
*A61K 31/352* (2006.01)
*A61K 31/683* (2006.01)
*A61K 31/685* (2006.01)
*A61K 45/06* (2006.01)

(52) U.S. Cl.
CPC .......... *A61K 31/685* (2013.01); *A61K 31/05* (2013.01); *A61K 31/352* (2013.01); *A61K 31/683* (2013.01); *A61K 45/06* (2013.01)

(58) Field of Classification Search
CPC .... A61K 31/05; A61K 31/352; A61K 31/685; A61K 31/683; A61K 45/06
See application file for complete search history.

(56) References Cited

U.S. PATENT DOCUMENTS

| | | | |
|---|---|---|---|
| 4,221,731 A | 9/1980 | Short et al. | |
| 4,399,224 A | 8/1983 | Filder et al. | |
| 4,479,977 A | 10/1984 | Dashiel et al. | |
| 4,608,267 A | 8/1986 | Dutilh | |
| 7,645,795 B2 | 1/2010 | Kane et al. | |
| 2005/0019423 A1 | 1/2005 | Kane et al. | |
| 2007/0042008 A1 | 2/2007 | Kane et al. | |
| 2007/0060639 A1* | 3/2007 | Wermeling | A61K 9/0043 514/454 |
| 2007/0203209 A1* | 8/2007 | Bartolini | A61K 31/33 514/367 |
| 2008/0254017 A1 | 10/2008 | Kane et al. | |

FOREIGN PATENT DOCUMENTS

| | | | |
|---|---|---|---|
| AT | 509000 A1 * | 5/2011 | ........... A23L 1/3002 |
| WO | WO 01/03696 | 1/2001 | |
| WO | WO 02/090534 | 11/2002 | |
| WO | WO 03/011873 | 2/2003 | |
| WO | WO2005/089269 | 9/2005 | |
| WO | PCT/US2015018217 | 7/2015 | |

OTHER PUBLICATIONS

Eastgate et al, :A Role for Manganese Superoxide Dismutase in Radioprotection of Hematopoietic Cells by Interleukin-1, Blood, vol. 81, pp. 639-646 (1993).
Kummerow et al.:"Effects of trans fats on prostacyclin production", Scand Scand Cardiovasc J. Dec. 2013;47(6):377-82.
Potier"Lipid blood profile in captive Brahminy kite as a possible indication of increased susceptibility to atherosclerosis" J Zoo Wildl Med. Sep. 2013;44(3):549-54.
Usher et al.:"Gut microbiota metabolism of I-carnitine and cardiovascular risk" Atherosclerosis. Dec. 2013;231(2):456-61.
Dessì:"Atherosclerosis, Dyslipidemia, and Inflammation" The Significant Role of Polyunsaturated Fatty Acids.ISRN Inflamm. May 12, 2013;2013:191823.
Shentu et al.:"The role of oxysterols in control of endothelial stiffness" J Lipid Res. Jul. 2012;53(7):1348-58.
Chrysohoou et al.:"Cardiovascular disease-related lifestyle factors and longevity" Cardiol Res Pract. 2011;2011:386892.
Dwight Lundell "Doctors Reverse Advice on Cholesterol and Heart Disease" (2011).
Sala-Vila et al: "Fatty acids in serum phospholipids and carotid intima-media thickness in Spanish subjects with primary dyslipidemia" Am J Clin Nutr. Jul. 2010;92(1):186-93.
Des "A defect in Δ6 and Δ5 desaturases may be a factor in the initiation andprogression of insulin resistance, the metabol" Lipids Health Dis. Nov. 9, 2010;9:130.
Degirolamo:"Dietary monounsaturated fatty acids appear not to provide cardioprotection" Curr Atheroscler Rep. Nov. 2010;12(6):391-6.
Cohn JS, et al.:"Dietary phospholipids and intestinal cholesterol absorption" Nutrients. Feb. 2010;2(2):116-27.
Daniels TF et al.:"Lipoproteins, cholesterol homeostasis and cardiac health" Int J Biol Sci. Jun. 29, 2009;5(5):474-88.
Das Un.:"Essential fatty acids and their metabolites could function as endogenous HMG-CoA reductase . . . " Lipids Health Dis. Oct. 15, 2008;7:37.
Ishikado A et al.:"Soy phosphatidylcholine inhibited TLR4-mdiated MCP-1 expression in vascular cells" Atherosclerosis. Aug. 2009;205(2):404-12.

(Continued)

*Primary Examiner* — Sarah Pihonak

(74) *Attorney, Agent, or Firm* — Houri Khalilian; Law Offices of Khalilian Sira, LLC

(57) ABSTRACT

This invention relates to compositions containing combinations of a balanced PC composition and one or more cannabinoids, a natural or synthetic derivative thereof, or a salt thereof, and kits containing such combinations and methods of using such combinations to treat subjects suffering from addiction to substances and related diseases or disorders. This invention also relates to the synergistic effect of such combination therapies in humans.

10 Claims, No Drawings

(56) References Cited

OTHER PUBLICATIONS

Das Un,;"Can endogenous lipid molecules serve as predictors and prognostic . . . " Prostaglandins Leukot Essen Fatty Acids 2007;76:251-268 Lipids Health Dis. May 20, 2008;7:19.

Brown JM et al."Monounsaturated fatty acids and atherosclerosis: opposing views from epidemiology . . . " Curr Atheroscler Rep. Dec. 2007;9(6):494-500.

Chung BH et al.:"Phosphatidylcholine-rich acceptors, but not native HDL or its apolipoproteins . . . " Biochim Biophys Acta. Mar. 21, 2005;1733(1):76-89.

Hajj Hassan et al.:"Structural modification of plasma HDL by phospholipids promotes efficient ABCA1-mediated cholesterol release" J Lipid Res. Jul. 2005;46(7):1457-65.

Olthof MR et al.:"Choline supplemented as phosphatidylcholine decreases fasting and postmethionine-loading plasma . . . " Am J Clin Nutr. Jul. 2005;82(1):111-7.

Navab M, et al.:"Oral synthetic phospholipid (DMPC) raises high-density lipoprotein cholesterol levels, . . . " Oct. 7, 2003;108(14):1735-9.

Shmeeda H et al.:"Heat acclimation in rats: modulation via lipid polyunsaturation" Am J Physiol Regul Integr Comp Physiol. Aug. 2002;283(2):R389-99.

Merkel M et al.:"Compared with saturated fatty acids, dietary monounsaturated fatty acids . . . " Proc Natl Acad Sci U S A. Nov. 6, 2001;98(23):13294-9.

Yancey PG et al:"High density lipoprotein phospholipid composition is a major determinant . . . " J Biol Chem. Nov. 24, 2000;275(47):36596-604.

He Y, Xu N, Liu X "The effect of phospholipid liposomes on atherosclerosis and serum lipid in rabbits]". [Article in ChineseZhonghua Nei Ke Za Zhi. May 1996;35(5):313-6.

Klimov AN et al.:"Essential phospholipids versus nicotinic acid in the treatment of patients . . . " Cardiovasc Drugs Ther. Dec. 1995;9(6):779-84.

Shmeeda H et al.:"Cholesterol distribution in rat heart myocytes" Am J Physiol. Feb. 1995;268(2 Pt 2):H759-66.

Heyden S"Polyunsaturated and monounsaturated fatty acids in the diet to prevent coronary heart disease via cholesterol reduction." Ann Nutr Metab. 1994;38(3):117-22.

Williams JS et al:"Low density lipoprotein receptor-independent hepatic uptake of a . . . " Proc Natl Acad Sci U S A. Jan. 1988;85(1)242-6.

Koizumi et al.:"Behavior of human apolipoprotein A-I: phospholipid and apoHDL:phospholipid complexes in vitro and after . . . ".J Lipid Res. Nov. 1988;29(11):1405-15.

Ovesen I. Etal: "The effects of oral soybean phospholipid on serum total cholesterol, plasma triglyceride . . . " JPEN J Parenter Enteral Nutr. Nov.-Dec. 1985;9(6):716-9.

\* cited by examiner

COMPOSITIONS AND METHODS FOR TREATING ADDICTION

CROSS REFERENCE TO RELATED APPLICATIONS

This application claims priority to U.S. Provisional Application No. 61/969,066, filed Mar. 21, 2014, the entire contents of which are incorporated herein by reference.

FIELD OF THE INVENTION

Described herein is a cannabinoid-based combination therapy suitable for local and systemic delivery to a mammal; compositions for delivering such pharmaceutically active agents and the use of such compositions in treating and preventing addiction and related diseases and disorders.

I. BACKGROUND OF THE INVENTION

Addiction is a dependence on a substance or behavior that the afflicted person is unable to control. Substance addictions can include for example alcoholism, drug abuse, and smoking whereas process addictions can include for example, gambling, spending, shopping, eating, and sexual activity.

Dependence upon drugs has serious and deleterious effects on the social, economic and medical condition of the addicted individual. The problem with substance addiction is prevalent in the world. In the United States, this problem is specifically compounded by the ease of access to several addictive substances such as, for example, nicotine, cocaine, amphetamine, methamphetamine, ethanol, heroin, morphine, phencyclidine (PCP), methylenedioxymethamphetamine (MDMA). These and other addictive substances are readily available and routinely used by large segments of the United States population. Indeed, by the age of 12, about 50% of adolescents have consumed alcohol, about 40% have smoked tobacco, and about 20% have smoked marijuana. Non-medical use of prescription pain relievers, sedatives, and stimulants is also on the increase.

Addiction is characterized by compulsive drug-seeking and use, even in the face of negative health consequences. There are several co-morbid pathologies related to the addictive abuse of illegal substances, which fall into different categories. Firstly, the high death index related to the toxic effects induced by the overdose of such substances. Secondly, the induction of teratogenic effects in the newborn, which are frequently associated to the chronic abuse of illegal substances by addicted pregnant mothers. Finally, the high incidence of co-morbid diseases of acquiring viral infections such as the human immunodeficiency virus (HIV), frequently detected in heroin abusers, as well as the increased rates of crimes, violence and delinquency frequently associated to the drug-trade and drug-intake of such illegal substances.

Several families of addictive drugs are in fact derived from natural plant sources. For example, cocaine is a naturally occurring nonamphetamine stimulant derived from the leaves of the coca plant, Erythroylon coca. Epidemiologically, the pyschostimulants such as cocaine and amphetamines, and to a lesser extent, opiate substances, like heroin and morphine, represent the most prevalent drugs causing the highest addictive morbidity worldwide.

The addictive liability of drugs of abuse, such as for example, cocaine, nicotine, methamphetamine, morphine, heroin, ethanol, phencyclidine, methylenedioxmethamphetamine or other drugs of abuse has been linked to their pharmacological actions on mesotelencephalic dopamine (DA) reinforcement/reward pathways in the central nervous system (CNS). Dopaminergic transmission within these pathways is modulated by gamma-amino butyric acid (GABA).

Alcohol abuse and alcohol dependency are also among the most serious types of addiction. Alcohol addiction can cause liver, pancreatic and kidney disease, heart disease, including dilated cardiomyopathy, polyneuropathy, internal bleeding, brain deterioration, alcohol poisoning, increased incidence of many types of cancer, insomnia, depression, anxiety, and even suicide. Heavy alcohol consumption by a pregnant mother can also lead to fetal alcohol syndrome, which is an incurable condition. Additionally, alcohol abuse and alcohol dependence are major contributing factors for head injuries, motor vehicle accidents, violence and assaults, and other neurological and other medical problems.

Dependence on nicotine is yet another progressive and prevalent type of addiction in both developed and underdeveloped countries around the world. The impact of nicotine addiction in terms of morbidity, mortality, and economic costs to society is enormous. Tobacco kills more than 430,000 U.S. citizens each year, more than alcohol, cocaine, heroin, homicide, suicide, car accidents, fire, and AIDS combined. Tobacco use is the leading preventable cause of death in the United States. Economically, an estimated $80 billion of total U.S. health care costs each year is attributable to smoking. However, this cost is well below the total cost to society because it does not include burn care from smoking-related fires, perinatal care for low-birth-weight infants of mothers who smoke, and medical care costs associated with disease caused by secondhand smoke. Taken together, the direct and indirect costs of smoking are estimated at $138 billion per year.

In the past, treatment of chemical dependence largely involved attempts to persuade patients to discontinue use of the substance voluntarily (behavioral therapy). However, cocaine, morphine, amphetamines, nicotine, and alcohol, and other types of dopamine-producing agents are highly addictive substances, and dependence upon such drugs can be harder to break and is significantly more damaging than dependence on most other addictive substances. In particular, alcohol, cocaine, and heroin dependence are typically chronic relapsing disorders.

Accordingly, there has been much interest in the scientific community in attempting to find substances that could be employed to ameliorate dependency on addictive agents. It is therefore clear that there has been and remains today a long standing need for compositions and methods to treat addiction and related diseases or disorders in a living human subject before the disease has manifested far enough to produce psychological changes, thereby allowing earlier and more effective therapeutic intervention. It would therefore be extremely beneficial if there were a way to provide a combination therapy that simultaneously provides amelioration or treatment of addiction or related diseases or disorder while at the same time simultaneously addressing other health issues related to depletion of phosphatidylcholine and increased sphingomyelin in cell membranes. Accordingly, there is a long felt need for discovering new compositions and methods that can achieve such therapeutic effects in patients with addiction or related disorders or diseases.

The present invention as disclosed and described herein provides methods and compositions for a combination therapy that can be used to treat or ameliorate addiction or related diseases or disorders while simultaneously correcting the impairment of cell membranes by correcting the ratio of phosphatidylcholine to sphingomyelin.

The present invention as disclosed and described herein provides methods and compositions for a combination therapy that can be used to treat or ameliorate addiction while simultaneously regulating fatty acid balance in cell membranes and reducing higher sphingomyelin to phosphatidylcholine ratios therein.

II. SUMMARY OF THE INVENTION

The present invention is directed to compositions and methods for treating addiction and related diseases and disorders in a subject in need thereof.

In its broadest aspect, a pharmaceutical composition for cannabinoid combination therapy is provided comprising: (a) a therapeutically effective amount of a first composition comprising a balanced PC composition; and (b) a therapeutically effective amount of a second composition comprising one or more cannabinoids, a natural or synthetic derivative thereof, or a salt thereof; wherein said first composition and said second composition are each administered together with a pharmaceutically acceptable carrier or diluent.

In one embodiment of the present invention, the balanced PC composition comprises Phosphotidylcholine (PC), Phosphotidylethanolamine (PE), Phosphatidyl inositol (PI), Phosphatidic Acid (PA), Phosphatidylglycerol (PG), Essential Fatty Acids C18.2 (omega 6) (linoleic acid), C18.3 (omega 3) (alpha linolenic acid) (in an approximate 4:1 ratio), or any combination thereof.

In another embodiment of the present invention, the balanced PC composition comprises phospholipids derived from a variety of plant and animal sources.

In one embodiment, a pharmaceutical composition for combination therapy is provided comprising: (a) a therapeutically effective amount of a first composition comprising a balanced PC composition; (b) a therapeutically effective amount of a second composition comprising one or more cannabinoids, an isolated natural or synthetic derivative thereof, or salt thereof; wherein said first composition and said second composition are each administered together with a pharmaceutically acceptable carrier or diluent.

In another aspect, a pharmaceutical composition is provided for the prevention, amelioration and/or treatment of symptoms of diseases related to impairment of development and activities of cells and tissues, and in particular, impairment of cell membranes, wherein the pharmaceutical composition comprises at least two compositions, a therapeutically effective amount of a first composition comprising a balanced PC composition and a therapeutically effective amount of a second composition comprising one or more cannabinoids, an isolated natural or synthetic derivative thereof, or salt thereof, in a suitable carrier or diluent.

Thus, in one embodiment, this invention is directed to composition comprising a first composition for use with a second composition for achieving an anti-addiction effect in a subject suffering from addiction to substances or behaviors, which effect by administering said first and second compositions separately wherein said first composition comprises a therapeutically effective amount of a balanced PC composition; and (b) a therapeutically effective amount of a second composition comprising one or more cannabinoids, a natural or synthetic derivative thereof, or a salt thereof, wherein said first composition and said second composition are each optionally and independently administered together with a pharmaceutically acceptable carrier or diluent.

In certain embodiments, said antiaddiction effect is manifested by a slowing of the progression of one or more symptoms or effects of addiction to substances or behaviors including, for example, and not by way of limitation, neuropsychiatric or neurological impairment, heart disease, cancer, cirrhosis, depression, seizures, aggression, anxiety, disturbed sleep, gastrointestinal side effects, sedation, skin effects, unconsciousness, convulsions, hallucinations, cardiac arrest, suffocation, respiratory depression, sleep disorders, digestive disorders, blackouts, extreme mood changes, changes in energy, weight loss or weight gain, or any combination thereof.

In one embodiment, the therapeutically effective amount of a first composition comprising a balanced PC composition and the therapeutically effective amount of a second composition comprising one or more cannabinoids, an isolated natural or synthetic derivative thereof, or salt thereof compositions are formulated in one or different solutions, are either singularly or both administered in a time-released manner, are either singularly or both administered in a dry formulation, liquid formulation, or are either singularly or both administered parenteraly, orally, transdermally, intranasally, intravenously, or using other routes of administration as described infra.

In one embodiment, the therapeutically effective amount of a first composition comprising a balanced PC composition and the therapeutically effective amount of a second composition comprising one or more cannabinoids, an isolated natural or synthetic derivative thereof, or salt thereof, are administered contemporaneously or are administered at different time intervals.

In another one embodiment, the therapeutically effective amount of a first composition comprising a balanced PC composition is administered in any order or is administered both prior to and after the therapeutically effective amount of a second composition comprising one or more cannabinoids, an isolated natural or synthetic derivative thereof, or salt thereof.

In a preferred embodiment, the therapeutically effective amount of a first composition comprising a balanced PC composition and the therapeutically effective amount of a second composition comprising one or more cannabinoids, an isolated natural or synthetic derivative thereof, or salt thereof, are administered to a subject in need thereof in a single dose semi-liquid packet.

In another aspect of the present invention, methods are provided for treating a subject at risk for developing symptoms of diseases related to impairment of development and activities of cells and tissues in order to delay the onset of the one or more of the aforementioned underlying symptoms related to addiction. The prevention, treatment and/or amelioration of one or more of the aforementioned symptoms related to addiction need not be complete, so long as at least one symptom of the disease is prevented, treated or ameliorated.

In one embodiment, this invention is also directed to a method for treating a subject who has been diagnosed as suffering from addiction and who is in need of therapeutic treatment comprising administering to said subject (a) a therapeutically effective amount of a first composition comprising a balanced PC composition; and (b) a therapeutically effective amount of a second composition comprising one or more cannabinoids, a natural or synthetic derivative thereof, or a salt thereof; wherein said first composition and said second composition are each optionally and independently administered together with a pharmaceutically acceptable carrier or diluent, and wherein said therapeutic treatment is prevention, treatment or amelioration of one or more symptoms of addiction.

III. DETAILED DESCRIPTION OF THE INVENTION

Reference now will be made in detail to embodiments of the invention. It will be apparent to those skilled in the art that various modifications and variations can be made in the present invention without departing from the scope or spirit of the invention. For instance, features illustrated or described as part of one embodiment, can be used on another embodiment to yield a still further embodiment.

In general, the present invention is directed to compositions and methods related to a combination therapy that ameliorates and/or treats addiction, through administration of a combination therapy comprising a first composition comprising a balanced PC composition in combination with a second composition comprising one or more cannabinoids.

The combination therapy of the present invention has unexpectedly completely circumvented the known deleterious side effects associated with the higher dose administration of cannabinoids by co-administration of a balanced PC composition and one or more cannabinoids, which in turn increases the bioavailability of this drug and its adsorption and passage through cell membranes and the blood brain barrier.

Cannabinoids such as, for example, *cannabis* or cannabidiol have been shown to be effective for modulation of tissue regeneration and development. There are, however, many side effects associated with *cannabis* and especially to the higher dosages of *cannabis*. Only about 1% of *cannabis* is reported to pass the blood brain barrier when administered alone intravenously.

By reducing or preventing the one or more side effects of the use of cannabinoids alone, the present invention provides a combination therapy of one or more cannabinoids with a balanced PC composition, wherein the overall therapeutic benefits described supra are increased considerably. Furthermore, the reduction or prevention of the side effects of cannabinoid use when administered in combination with a balanced PC composition provides an unexpected synergistic benefit.

The unexpected synergistic effects of the balanced PC composition cannabinoid combination therapy of the present invention include, for example, and not by way of limitation, i) reducing the oxidative stress of free radicals and increasing cellular homeostasis resulting from synergistically increasing the bioavailability of one or more cannabinoids; ii) inhibiting the formation of cholesteryl esters derived from LDL or other synthesis and increasing efflux of cholesterol from the cells by decreasing available cholesterol for esterification as a result of synergistically increasing the bioavailability of both endogenous and exogenous cannabinoids; iii) inhibiting the progression of atherosclerotic plaque and significantly reducing arterial plaque through modulation and synergistically increasing the bioavailability of both endogenous and exogenous cannabinoids; and iv) acting as a smooth muscle relaxant, relaxing arterial walls (vasodilatation), lowering blood pressure, and increasing blood flow and circulation by synergistically increasing the bioavailability of cannabinoids.

In general, a balanced PC composition of the present invention provides the following beneficial characteristics: i) enhanced PC concentration; ii) improved solubility and stability of PC; iii) Improved bioavailability of PC; iv) improved targeting cell membrane capability in vivo and hence enhanced immunological benefit (a balanced PC composition has an enhanced glycoprotein concentration and hence increased capability to provide additional receptors via attachment to cell membranes in vivo); v) having a reduced concentration of integral carbohydrates including glycolipids, galactose, etc.; vi) having a reduced concentration of undesirable lipids including, for example, sphingomyelin; vii) having an improved concentration of the essential fatty acids and a balanced ratio of linoleic acid and alpha linolenic acid (in an approximate 4:1 ratio); and viii) having a range of beneficial minerals and electrolytes in a specific concentration range; and xi) having an improved ability for liposome mediated-transport of drugs or any combination thereof. These balanced PC composition benefits synergistically combine together with the one or more cannabinoids in the balanced PC cannabinoid composition combination therapy utilized in the compositions and methods of the present invention to provide one or more of the therapeutic benefits described herein.

In one embodiment, the balanced PC composition cannabinoid compositions and methods prepared according to the present invention provide a suspension of liposomes containing substantially more phosphatidylcholine than the available competing phosphatidyl products.

In another embodiment, the liposomes produced by the methods of the present invention are small unilamellar vesicles (SUVs) having sizes predominantly between 0.02 and 0.1 microns, and are composed predominantly or exclusively of a balanced PC composition with the one or more cannabinoids entrapped there within.

Without intending to be limited to a particular mechanism of action, it is believed that the administration of a balanced PC composition in combination with an one or more exogenous cannabinoids serves to synergistically regulate and promote the aforementioned physiological homeostasis in the endocannabinoid system by leading to a decrease in the relative sphingomyelin to phosphatidylcholine mass ratio which in turn synergistically allows the endogenous cannabinoid system to modulate the severity and/or duration of addiction through activation of the CB1 receptor.

Components of the Composition of the Combination Therapy

1. Components of First Composition BodyBio PC 1.1 Phosphatidylcholine

Phosphatidylcholine (PC) is the predominant phospholipid of all cell membranes and of the circulating blood lipoproteins. Of the tens of thousands of molecules that make up the life of a cell, Phosphatidylcholine (PC) stands apart; probably the most important one of all. PC is the main lipid constituent of the lipoprotein particles circulating in the blood and the preferred precursor for certain phospholipids and other biologically important molecules. PC also provides antioxidant protection in vivo. In animal and human studies, PC protected against a variety of chemical toxins and pharmaceutical adverse effects.

Chemically, PC is a glycerophospholipid that is built on glycerol ($CH_2OH$—$CHOH$—$CH_2OH$) and substituted at all three carbons. Carbons I and 2 are substituted by fatty acids and carbon 3 by phosphorylcholine. Simplistically, the PC molecule consists of a head-group (phosphorylcholine), a middle piece (glycerol), and two tails (the fatty acids, which vary). Variations in the fatty acids in the tails account for the great variety of PC molecular species in human tissues.

In vivo, PC is produced via two major pathways. In the predominant pathway, two fatty acids (acyl "tails") are added to glycerol phosphate (the "middle piece"), to generate phosphatidic acid (PA) that is converted to diacylglycerol, after which phosphocholine (the "head-group") is added on from CDP-choline. The second, minor pathway is phosphatidylethanolamine (PE) methylation, the PEMT pathway, in which the phospholipid PE has three methyl groups added to its ethanolamine head-group, thereby converting it into PC.

In one embodiment, the PC component of the balanced PC composition cannabinoid combination therapy of the present invention may be derived from any and all lecithin-based raw materials, for which the phosphatides have been rendered water soluble by one of the many previously published fluidizing methods, for example, Short, U.S. Pat. No. 4,221,731 1980, Flider, U.S. Pat. No. 4,399,224 1983, the entire disclosures of each of which are specifically incorporated by reference herein, and those commercial suppliers of raw lecithin such as, for example, and not by way of limitation, Archer Daniels Midland (ADM), Cargill, Bunge, Solae, American Lecithin, or any plant lecithin or animal lecithin including for example, and not by way of limitation, egg, or any combination thereof.

In another embodiment, the PC component of the balanced PC composition cannabinoid combination therapy comprises phosphatidylcholine derived from soy.

In another embodiment, the first composition of the present invention is a balanced PC composition which is specifically available from BodyBio Inc. (referred to hereinafter as "BodyBio PC" "BodyBio balanced PC" or "balanced PC"). The concentration of PC in BodyBio PC for administration ranges from about 100 mg to about 10,000 mg. In one embodiment, the concentration range of PC is from about 200 mg to about 5000 mg. In another embodiment, the concentration range of PC is from about 300 mg to about 3000 mg. In a preferred embodiment of the invention, the concentration range of PC is from about 500 mg to about 1000 mg.

In one embodiment, the total amount of phospholipids in BodyBio PC is about 61%, which is about 9% higher than competitive PC products (i.e., approximately 61% versus about 52%). In one embodiment, total amount of phosphatidylcholine in BodyBio PC is approximately 29%, which is about 11-16% higher than competitive PC products such as for example, and not by way of limitation, that found with lecithin supplied by Dupont and ADM (i.e., about 29% versus about 18%). The percentages recited herein for the differences between BodyBio PC and competitive PC products are approximations only and are thus intended to include percentages that are up to 10% lower or 10% higher than the recited value, and all integer values there between.

In one embodiment, for example, and not by way of limitation, the fatty acids and phospholipid concentration in the intermediate phosphatidylcholine compound is presented below (including any combinations thereof). These percentage values provided below represent a non-limiting example of fatty acid content and of the various phospholipids found in the composition. The percentages recited herein are approximate and are intended to include percentages that are up to 10% lower or 10% higher than the recited value.

Fatty Acid Content:
C16.0 16.1%
C16.1 0.1%
C18.0 4.1%
C18.1 10.0%
C18.2 55.30% (omega 6)
C18.3 14.0% (omega 3)
C22.0 0.4%

Phospholipids:
Phosphotidylcholine (PC): about 29%
Phosphotidylethanolamine (PE): about 16%
Phosphatidyl inositol (PI): about 9%
Phosphatidic Acid (PA): about 4%
Phosphatidylglycerol (PG): about 1%
Total Phospholipids: about 61%

BodyBio PC contains a ratio of about 4 parts linoleic acid to about 1 part alpha linolenic acid. Most lecithin produced from soy has an essential fatty acid ratio of approximately 10-12:1.

BodyBio balanced PC is composed of phosphatides that are amphiphilic and automatically form bilipid membranes (liposomes) or unilipid membranes (micelles). Lecithin may contain the desired health providing phosphatides, however, in contrast to BodyBio balanced PC, the phospholipids derived from lecithin are generally oil based, which make them only suitable as an emulsifying agent for foods and cosmetics. Oil-based phosphatides are not amphiphilic, they have lost the necessary hydrophobic reaction to form a liposomal membrane and thus are incapable of integration into cell membranes and add to internal nutritional support system.

The increased level of available phospholipids in the balanced PC composition of the present invention is a significant improvement over the competitive PC products. The balanced PC compositions of the present invention have the unique advantage of containing phosphatidyl ethanolamine (PE), which has recently been found to be a necessary phospholipid in the membranes of mitochondria for the production of energy.

Thus, in one embodiment of the present invention, the balanced PC composition of the present invention comprises Phosphotidylcholine (PC), Phosphotidylethanolamine (PE), Phosphatidyl inositol (PI), Phosphatidic Acid (PA), Phosphatidylglycerol (PG), Essential Fatty Acids comprising C18.2 (omega 6) (linoleic acid) C18.3 (omega 3) (alpha linolenic acid)(in an approximate 4:1 ratio for the essential fatty acids or EFAs), or any combination thereof.

Mitochondrial membranes are enriched in phospholipids and proteins that are required for mitochondrial biogenesis and for maintenance of mitochondrial morphology and the tubular network. The two non-bilayer forming mitochondrial phospholipids cardiolipin (CL) (CL3) and phosphatidylethanolamine (PE) are required to maintain tubular mitochondrial morphology and are known to have overlapping functions in mitochondrial fusion. Although cells lacking CL or mitochondrial PE are viable, the loss of both phospholipids is lethal.

2. Cannabinoids for Use in the Second Composition

The compositions of the combination therapy of the present invention include as the second composition one or more cannabinoids, an isolated natural or synthetic derivative thereof, or salt thereof. Cannabinoids are a heteromorphic group of chemicals that act on cannabinoid receptors on cells that repress neurotransmitter release in the brain. These receptor proteins include the endocannabinoids (produced naturally in the body by humans and animals), the phytocannabinoids (found in *cannabis* and some other plants), and synthetic cannabinoids (manufactured chemically). The most notable cannabinoid is the phytocannabinoid Δ9-tetrahydrocannabinol (THC), the primary psychoactive compound of *cannabis*. Cannabidiol (CBD) is another major constituent of the plant, representing up to 40% in extracts of the plant resin. There are at least 85 different cannabinoids isolated from *cannabis*, exhibiting varied effects. Synthetic cannabinoids encompass a variety of distinct chemical classes: the classical cannabinoids structurally related to THC, the nonclassical cannabinoids (cannabimimetics) including the aminoalkylindoles, 1, 5-diarylpyrazoles, quinolines, and arylsulphonamides, as well as eicosanoids related to the endocannabinoids.

Cannabinoids according to this invention can either be exogenic or endogenic in origin. Exogenic cannabinoids can be both natural, (i.e. Phytocannabinoids derived from the *cannabis* plant itself) and synthetic (i.e. Marinol, Sativex, etc.) These exogenic cannabinoids can be both binding, aka agonists (i.e. THC the main psychoactive compound) and non-binding, aka antagonists (i.e., the non-psychoactive cannabinoids CBD, CBN, CBG, etc.) to endogenous cannabinoid receptors in vivo. Endogenic cannabinoids (i.e. Anandamide, 2-AG, etc.) and endogenous receptors sites (i.e. CB1 and CB2) are found throughout the body and regulate homeostasis in a wide variety of physiological and neurological functions from birth till death. Endocannabinoids are found in the human placenta and even breast milk and are essential to all the body's regulatory functions.

Endocannabinoids are lipid derived mediators which can be activated, stored, and synthesized from the cell membranes phospholipid's bilayer through multiple pathways, although complete understanding of the transport system needs further study. Endocannabinoid production can be increased by the introduction of extracellular stimuli (i.e., the ingestion or introduction of exogenic cannabinoids). The phospholipid bilayer, along with its many other functions, plays a central role in the Endocannabinoid System. A healthy phospholipid bilayer is therefore essential to a healthy Endocannabinoid system (ECS) and vice versa: the phospholipid bilayer and the ECS work together synergistically to regulate and promote physiological homeostasis. The ECS and its regulatory processes are extremely sensitive to the quality and structure of the phospholipid bilayer. This relationship and the synergistic effects thereto are enhanced and exploited by using the balanced PC cannabinoid combination therapeutic treatments of the invention as described herein to achieve a further synergistic effect which is much greater than the additive value expected by combination of a balanced PC composition and cannabinoids.

What follows is a non-limiting listing of the cannabinoids that may be used in the combination therapy compositions and methods of the present invention.

2.1 *Cannabis*-Derived Cannabinoids 2.1.1 *Cannabis, Sativa, Indica* Plant *Ruderalis* and Hybrids Thereof The *Cannabis* plant, a genus of dioeciously flowering plants, has been divided into three distinct species: *Cannabis Sativa, Cannabis Indica*, and *Cannabis Ruderalis*. Phytocannabinoids (i.e., THC, CBD, CBN, CBG, etc.) can be extracted through various methods and have been used in medicinal compositions for thousands of years by many different cultures around the world for a wide range of symptoms and ailments.

The classical cannabinoids are concentrated in a viscous resin produced in structures known as glandular trichomes. At least 85 different cannabinoids have been isolated from the *Cannabis* plant. The best studied cannabinoids include tetrahydrocannabinol (THC), cannabidiol (CBD) and cannabinol (CBN).

Despite the huge variety of marijuana available, almost all ultimately come from two *cannabis* family species. These two essential species are known as *Cannabis sativa* and *Cannabis Indica* and they differ fundamentally in their chemical composition and medical applications. *Cannabis Ruderalis* a.k.a. industrial hemp is the third species and interest in this species is gaining momentum at the moment because it is high in the non-psychoactive cannabinoid CBD and contains only trace amounts of 1% or less the psychoactive cannabinoid.

2.2.1 Types of Cannabinoids

All classes derive from cannabigerol-type compounds and differ mainly in the way this precursor is cyclized. The classical cannabinoids are derived from their respective 2-carboxylic acids (2-COOH) by decarboxylation (catalyzed by heat, light, or alkaline conditions) include the following: CBG (Cannabigerol); CBC (Cannabichromene); CBL (Cannabicyclol); CBV (Cannabivarin); THCV (Tetrahydrocannabivarin); CBDV (Cannabidivarin); CBCV (Cannabichromevarin); CBGV (Cannabigerovarin); CBGM (Cannabigerol Monomethyl Ether); and Tetrahydrocannabinol.

2.2.2 Tetrahydrocannabinol

Tetrahydrocannabinol (THC) is the primary psychoactive component of the *Cannabis* plant. Delta-9-tetrahydrocannabinol ($\Delta$9-THC, THC) and delta-8-tetrahydrocannabinol ($\Delta$8-THC) mimic the action of anandamide, a neurotransmitter produced naturally in the body. These two THC's produce the effects associated with *cannabis* by binding to the CB1 cannabinoid receptors in the brain. THC appears to ease moderate pain (analgesic) and to be neuroprotective. Studies show THC reduces neuroinflammation and stimulates neurogenesis. THC has approximately equal affinity for the CB1 and CB2 receptors. Its effects are perceived to be more cerebral.

2.2.2.1 Sources of THC

The *Indica* and *Sativa* subspecies differ in their medicinal properties. *Sativa* strains produce more of a euphoric high, lifting the consumer's mood and therapeutically relieving stress. *Indica* strains relax muscle and work as general analgesics, also helping with sleep. A cancer patient hoping to relieve the pain from chemotherapy would benefit greatly from the effects of an *Indica* plant bud, whereas an individual dealing with depression would better benefit from an extract from *Sativa* plant. *Sativa*'s has low or no CBD levels. *Indica*'s chemical profile shows a more balanced mix, with moderate THC levels and higher levels of CBD. Differences in the chemical composition of *Cannabis* varieties may produce different effects in humans. Synthetic THC, called dronabinol (Marinol), does not contain CBD, CBN, or other cannabinoids, which is one reason why its pharmacological effects may differ significantly from those of natural *Cannabis*. Hybridization and crosses of all three exists and are of particular interest, especially if breeding for certain cannabinoid percentage profiles. (i.e., High THC/High CBD, Low THC/High CBD).

2.2.3 Cannabidiol

Cannabidiol (CBD) is not psychoactive, and was thought not to affect the psychoactivity of THC. However, recent evidence shows that smokers of *cannabis* with a higher CBD/THC ratio were less likely to experience schizophrenia-like symptoms. Cannabidiol has little affinity for CB11 and CB2 receptors but acts as an indirect antagonist of cannabinoid agonists. It is an antagonist at the putative new cannabinoid receptor, GPR55, a GPCR expressed in the caudate nucleus and putamen. Cannabidiol has also been shown to act as a 5-HT1A receptor agonist, an action that is involved in its antidepressant, anxiolytic, and neuroprotective effects. It appears to relieve convulsion, inflammation, anxiety, and nausea. CBD has a greater affinity for the CB2 receptor than for the CB1 receptor. CBD shares a precursor with THC and is the main cannabinoid in low-THC *Can-* nabis strains. CBD apparently plays a role in preventing the short-term memory loss associated with THC in mammals.

2.2.4 Cannabinol

Cannabinol (CBN) is the primary product of THC degradation, and there is usually little of it in a fresh plant. CBN content increases as THC degrades in storage, and with exposure to light and air. It is only mildly psychoactive. Its affinity to the CB2 receptor is higher than for the CB1 receptor.

2.2.5 Cannabigerol

Cannabigerol (CBG) is non-psychotomimetic but still affects the overall effects of *Cannabis*. It acts as an a2-adrenergic receptor agonist, 5-HT1A receptor antagonist, and CB1 receptor antagonist. It also binds to the CB2 receptor.

2.2.6 Tetrahydrocannabivarin

Tetrahydrocannabivarin (THCV) is prevalent in certain central Asian and southern African strains of *Cannabis*. It is an antagonist of THC at CB1 receptors and attenuates the psychoactive effects of THC.

2.2.7 Cannabidivarin

Although cannabidivarin (CBDV) is usually a minor constituent of the cannabinoid profile, enhanced levels of CBDV have been reported in feral *cannabis* plants from the northwest Himalayas, and in hashish from Nepal.

2.2.8 Cannabichromene

Cannabichromene (CBC) is non-psychoactive and does not affect the psychoactivity of THC. Cannabichromene is more common in tropical *cannabis* varieties. Effects include anti-inflammatory and analgesic. THC It is found in nearly all tissues in a wide range of animals. Two analogs of anandamide, 7,10,13,16-docosatetraenoylethanolamide and "homo"-y-linolenoylethanolamine, have similar pharmacology. All of these are members of a family of signaling lipids called "N"-acylethanolamides, which also includes the non-cannabimimetic palmitoylethanolamide and oleoylethanolamine, which possess anti-inflammatory and orexigenic effects, respectively. Many "N"-acylethanolamines have also been identified in plant seeds and in molluscs.

2.2.9 Cannabicyclol

Cannabicyclol (CBL) is a non-psychoactive cannabinoid found in the *cannabis* species. CBL is a degradative product like Cannabinol. Light converts Cannabichromene to CBL and it contains 16 stereoisomer.

2.2.10 Cannabivarin

Cannabivarin (CBV) is a non-psychoactive cannabinoid found in minor amounts in *cannabis* plant. It is an analog of cannabinol (CBN). Cannabivarin is an oxidation product of Tetrahydrocannabivarin (THCV)

2.3 Other Phytocannabinoids

The compositions of the present invention may also utilize phytocannabinoids from several other several plant species besides *cannabis*. These include *Echinacea purpurea, Echinacea angustifolia, Echinacea pallida, Acmella oleracea, Helichrysum umbraculigerum*, and *Radula marginata*. The best known cannabinoids that are not derived from *Cannabis* are the lipophilic alkamides (alkylamides) from *Echinacea* species. At least 25 different alkylamides (dodeca-2E,4E,8Z,10E/Z-tetraenoic-acid-isobutylamides) have been identified, and some of them have shown affinities to the CB2-receptor. In *Echinacea* species, cannabinoids are found throughout the plant structure, but are most concentrated in the roots and flowers. Yangonin found in the Kava plant is a ligand on the CB1 receptor. Tea (*Camellia sinensis*) catechins have an affinity for human cannabinoid receptors. A wide spread dietary cannabinoid, beta-caryophyllene, a component from the essential oil of *cannabis* and other medicinal plants, has also been identified as a selective agonist of peripheral CB2-receptors, in vivo.

2.4 Synthetic Cannabinoids

In addition to the natural cannabinoids described above for use in the second composition of the present invention, synthetic cannabinoids may also be used. One of ordinary skill in the art can readily synthesize numerous synthetic cannabinoids for use in the compositions and methods of the present invention. Non-limiting representative examples of such synthetic cannabinoids include, for example, Dronabinol (Marinol) (Δ9-tetrahydrocannabinol (THC)), used as an appetite stimulant, anti-emetic, and analgesic; Nabilone (Cesamet), a synthetic cannabinoid and an analog of Marinol; Sativex, a cannabinoid extract oral spray containing THC, CBD, and other cannabinoids used for neuropathic pain and spasticity in 22 countries including England, Canada and Spain; and Rimonabant (SR141716), a selective cannabinoid (CB1) receptor inverse agonist once used as an anti-obesity drug under the proprietary name Acomplia.

2.5 Endocannabinoids

The endogenous cannabinoid system (ECS) is perhaps the most important physiological system involved in establishing and maintaining human health through homeostasis. Found throughout the body the ECS endocannabinoids serve as intercellular lipid messengers. Although in this intracellular signaling role they are similar to the well-known monoamine neurotransmitters, such as acetylcholine and dopamine, endocannabinoids differ in numerous ways from them. For instance, they use retrograde signaling. Non limiting examples of endocannabinoids that may be modulated by the compositions and methods of the present invention include, for example, those endocannabioids listed below.

2.5.1 N-Arachidonoylethanolamine

N-arachidonoylethanolamine (AEA), also known as Anandamide, is an endogenous cannabinoid neurotransmitter. It is synthesized from N-arachidonoyl phosphatidylethanolamine by multiple pathways. It is degraded primarily by the fatty acid amide hydrolase (FAAH) enzyme, which converts anandamide into ethanolamine and arachidonic acid. Inhibitors of FAAH lead to elevated anandamide levels and are being pursued for therapeutic use and treatments. Anandamide's effects can be either central, in the brain, or peripheral, in other parts of the body. These effects are mediated by the CB1 receptors in the CNS, and the CB2 receptors in the periphery, which is involved in homeostasis and functions of the immune system.

2.5.2 2-Arachidonoyl Glycerol (2-AG)

Another endocannabinoid, 2-arachidonoyl glycerol, binds to both the CB1 and CB2 receptors with similar affinity, acting as a full agonist at both, and there is some controversy over whether 2-AG rather than anandamide is chiefly responsible for endocannabinoid signaling in vivo. In particular, one in vitro study suggests that 2-AG is capable of stimulating higher G-protein activation than anandamide, although the physiological implications of this finding are not yet known.

2.5.3 2-Arachidonyl Glyceryl Ether (Noladin Ether)

Endocannabinoid, 2-arachidonyl glyceryl ether (noladin ether), is isolated from porcine brain. Previously, it had been synthesized as a stable analog of 2-AG; indeed, some controversy remains over its classification as an endocannabinoid, as another group failed to detect the substance at "any appreciable amount" in the brains of several different mammalian species. Noladin ether binds to the CB1 cannabinoid receptor ("K"i=21.2 nmol/L) and causes sedation, hypothermia, intestinal immobility, and mild antinociception in mice. It binds primarily to the CB1 receptor, and only weakly to the CB2 receptor. Like anandamide, NADA is also an agonist for the vanilloid receptor subtype 1 (TRPV1), a member of the vanilloid receptor family.

2.5.4 Virodhamine (OAE)

Virodhamine, or "0"-arachidonoyl-ethanolamine (OAE), is a full agonist at CB2 and a partial agonist at CB1, although it behaves as a CB1 antagonist "in vivo". In rats, Virodhamine was found to be present at comparable or slightly lower concentrations than anandamide in the brain, but 2- to 9-fold higher concentrations peripherally.

2.5.5 Function of Endocannabinoids

Endocannabinoids serve as intercellular 'lipid messengers', signaling molecules that are released from one cell and activate the cannabinoid receptors present on other nearby cells. Although in this intercellular signaling role they are similar to the well-known monoamine neurotransmitters, such as acetylcholine and dopamine, endocannabinoids differ in numerous ways from them. For instance, they use retrograde signaling. Furthermore, endocannabinoids are lipophilic molecules that are not very soluble in water. They are not stored in vesicles, and exist as integral constituents of the membrane bilayers that make up cells. They are believed to be synthesized 'on-demand' rather than made and stored for later use. The mechanisms and enzymes underlying the biosynthesis of endocannabinoids remain elusive and continue to be an area of active research. The endocannabinoid 2-AG has been found in bovine and human maternal milk.

2.5.6 Retrograde Signal

Conventional neurotransmitters are released from a 'presynaptic' cell and activate appropriate receptors on a 'postsynaptic' cell, where presynaptic and postsynaptic designate the sending and receiving sides of a synapse, respectively. Endocannabinoids, on the other hand, are described as retrograde transmitters because they most commonly travel 'backwards' against the usual synaptic transmitter flow. They are, in effect, released from the postsynaptic cell and act on the presynaptic cell, where the target receptors are densely concentrated on axonal terminals in the zones from which conventional neurotransmitters are released. Activation of cannabinoid receptors temporarily reduces the amount of conventional neurotransmitter released. This endocannabinoid mediated system permits the postsynaptic cell to control its own incoming synaptic traffic. The ultimate effect on the endocannabinoid-releasing cell depends on the nature of the conventional transmitter being controlled. For instance, when the release of the inhibitory transmitter GABA is reduced, the net effect is an increase in the excitability of the endocannabinoid-releasing cell.

3. Compositions and Therapeutic Methods for Treating Addiction

The novel combination of a balanced PC composition with one or more cannabinoids, which are synergistic when used in combination, results in easy delivery of and passage of a balanced PC composition and cannabinoids through the cell membrane and the blood brain barrier to support tissue regeneration, to inhibit the inflammatory reactions and to promote cerebral reperfusion.

Thus, in one embodiment, this invention is directed to a first composition for use with a second composition for achieving an anti-addiction effect in a human subject suffering from substance addiction wherein said first composition comprises (a) a therapeutically effective amount of a first composition comprising a balanced PC composition; and (b) a therapeutically effective amount of a second composition comprising one or more cannabinoids, a natural or synthetic derivative thereof, or a salt thereof, wherein said first composition and said second composition are each optionally and independently administered together with a pharmaceutically acceptable carrier or diluent.

In certain embodiments, said anti-addictive effect is manifested by a slowing of the progression of one or more of the aforementioned symptoms or effects of addiction to substances listed supra.

In yet another embodiment, this invention is directed to a first composition for use with a second composition for achieving an anti-alcohol addiction effect in a subject suffering from alcohol addiction, wherein said first composition comprises (a) a therapeutically effective amount of a first composition comprising a balanced PC composition; and (b) a therapeutically effective amount of a second composition comprising one or more cannabinoids, a natural or synthetic derivative thereof, or a salt thereof, wherein said first composition and said second composition are each optionally and independently administered together with a pharmaceutically acceptable carrier or diluent.

In certain embodiments, said anti-alcohol addiction effect is manifested by a slowing of the progression of one or more symptoms or effects of addiction to alcohol including, for example, and not by way of limitation, disturbed sleep, nausea, and vomiting, dizziness and talkativeness, hangovers, aggressive acts, including domestic violence and child abuse, difficulty walking, blurred vision, slurred speech, slowed reaction times, impaired memory, cognitive impairment, inhibition of neurogenesis, brain damage, brain shrinkage, blackouts, cirrhosis, alcohol-induced damage of the heart muscle (i.e., cardiomyopathy), and nerve damage (i.e., peripheral neuropathy), Wernicke-Korsakoff syndrome (WKS) (subjects prone to it if have thiamine deficiency), Wernicke's encephalopathy Korsakoff's psychosis, hepatic encephalopathy, fetal alcohol syndrome (FAS), neuropsychiatric or neurological impairment including severe anxiety, tremors, hallucinations, hypertension and convulsions, major depression, dysthymia, mania, hypomania, panic disorder, and phobias, malnutrition, alcoholic liver disease, pancreatitis, cardiovascular diseases including coronary heart disease, and ischemic stroke, liver disease, brain damage, or any combination thereof.

In yet another embodiment, this invention is also directed to a first composition for use with a second composition for achieving an anti-nicotine addiction effect in a subject suffering from nicotine addiction, which effect is achieved by administering said first and second compositions separately wherein said first composition comprises (a) a therapeutically effective amount of a first composition comprising a balanced PC composition; and (b) a therapeutically effective amount of a second composition comprising one or more cannabinoids, a natural or synthetic derivative thereof, or a salt thereof, wherein said first composition and said second composition are each optionally and independently administered together with a pharmaceutically acceptable carrier or diluent.

In certain embodiments, said anti-nicotine addiction effect is manifested by a slowing of the progression of one or more symptoms or effects of addiction to nicotine including, for example, and not by way of limitation, loss of sense of smell and taste, exacerbation of asthma symptoms, chronic obstructive pulmonary diseases, cardiovascular diseases, including stroke, heart attack, vascular disease, aneurysm, increases blood pressure and heart rate, leukemia, cataracts, and pneumonia; lung cancer, lung diseases, such as bronchitis and emphysema; induction of potentially atherogenic genes in human coronary artery endothelial cells, microvascular injury, teratogenic effects, an increased risk of Alzheimer's disease and schizophrenia, or any combination thereof.

In yet another embodiment, this invention is also directed to a first composition for use with a second composition for achieving an anti-prescription drug addiction effect in a subject suffering from prescription drug addiction, which effect is achieved by administering said first and second compositions separately wherein said first composition comprises (a) a therapeutically effective amount of a first composition comprising a balanced PC composition; and (b) a therapeutically effective amount of a second composition comprising one or more cannabinoids, a natural or synthetic derivative thereof, or a salt thereof, wherein said first composition and said second composition are each optionally and independently administered together with a pharmaceutically acceptable carrier or diluent.

In certain embodiments, said anti-prescription drug addiction effect is manifested by a slowing of the progression of one or more symptoms or effects of addiction to prescription drugs including, for example, and not by way of limitation, drowsy or intoxicated appearance, confusion about surroundings or time, unsteady movements and/or mannerisms, involuntary gestures, movements or tics, rapid, involuntary eye movement, poor judgment and decision-making, difficulty with memory, extreme agitation or irritability, irregular heartbeat, high blood pressure, elevated body temperatures not explained by environment or physical activity, seizures, cardiovascular failure, increasing hostility, feelings of paranoia, insomnia, which may persist for days at a time, unexplained weight loss (which can also indicate an eating disorder such as anorexia nervosa or bulimia), depression, rapid decrease in blood pressure not explained by other medical conditions, disorientation or confusion in familiar surroundings, constipation or other digestive irregularities, shortness of breath, cold flashes, regardless of environment, involuntary leg movements ("kicking"), restlessness, sharp bone and muscle pains, vomiting, diarrhea, cardiac arrest, seizures, mixing alcohol with prescription medications to accentuate the feeling of euphoria, changing sleep patterns, increasing irritability, or any combination thereof.

In yet another embodiment, this invention is also directed to a first composition for use with a second composition for achieving an anti-morphine, anti-cocaine, or anti-heroine addiction effect in a subject suffering from morphine, cocaine or heroin addiction, which effect is achieved by administering said first and second compositions separately wherein said first composition comprises (a) a therapeutically effective amount of a first composition comprising a balanced PC composition; and (b) a therapeutically effective amount of a second composition comprising one or more cannabinoids, a natural or synthetic derivative thereof, or a salt thereof, wherein said first composition and said second composition are each optionally and independently administered together with a pharmaceutically acceptable carrier or diluent.

In certain embodiments, said anti-morphine addiction effect is manifested by a slowing of the progression of one or more symptoms or effects of addiction to morphine including, for example, and not by way of limitation, slow breathing, lowered heart rate, dopiness, constipation, euphoria, itchiness, unconsciousness, cardiac arrest, suffocation due to lack of breathing and coma, cold, clammy skin, low blood pressure, slow pulse rate, shallow breathing, feeling faint or dizzy, confusion, constricted pupils, loss of normal muscle tension, cardiac arrest, circulatory collapse, sweating, chills, tearing eyes, runny nose, restlessness, muscle aches, backache, dilated pupils, irritability, trouble sleeping, high blood pressure, rapid heart rate, vomiting, nausea, abdominal cramps, constipation diarrhea, dry mouth, restlessness, muscle and bone pain, insomnia, diarrhea, and cold flashes with goose bumps ("cold turkey"), sedation, skin changes, warmth, flushing and urticaria or allergic eruptions, hypothermia, shrunken pupils, respiratory depression, hallucinations, delirium, dizziness and confusion, headache, memory loss, biliary colic, muscle rigidity, and myoclonus (abnormal movement of the limbs and muscles), or any combination thereof.

In certain embodiments, said anti-cocaine addiction effect is manifested by a slowing of the progression of one or more symptoms or effects of addiction to cocaine including, for example, and not by way of limitation, euphoria or feeling high, craving, an increasing sense of energy and alertness, an extremely elevated mood, a feeling of supremacy, irritability, paranoia, restlessness, anxiety, dilated pupils, high levels of energy and activity, excited, exuberant speech, nasal perforation, seizures, bizarre or violent behavior, arrhythmia, heart attack, permanent lung damage, ulcers, perforation of the stomach or intestines, rhabdomyolysis, impaired sexual function or any combination thereof.

In certain embodiments, said anti-heroin addiction effect is manifested by a slowing of the progression of one or more symptoms or effects of addiction to heroin including, for example, and not by way of limitation, shortness of breath, dry mouth, constricted (small) pupils, sudden changes in behavior or actions, disorientation, cycles of hyper alertness followed by sleep, droopy appearance, distant field of vision, substantial increases in time spent sleeping, increase in slurred, garbled or incoherent speech, weight loss, runny nose (not explained by other illness or medical condition), or any combination thereof.

In yet another embodiment, this invention is also directed to a first composition for use with a second composition for achieving an anti-food or anti-sex addiction effect in a subject suffering from food or sex addiction, which effect is achieved by administering said first and second compositions separately wherein said first composition comprises (a) a therapeutically effective amount of a first composition comprising a balanced PC composition; and (b) a therapeutically effective amount of a second composition comprising one or more cannabinoids, a natural or synthetic derivative thereof, or a salt thereof, wherein said first composition and said second composition are each optionally and independently administered together with a pharmaceutically acceptable carrier or diluent.

In certain embodiments, said anti-food addiction effect is manifested by a slowing of the progression of one or more symptoms or effects of addiction to food including, for example, and not by way of limitation, bulimia and anorexia, gorging in more food than one can physically tolerate, eating to the point of feeling ill, decreased energy, chronic fatigue, difficulty concentrating, sleep disorders, such as insomnia or oversleeping, restlessness, irritability, headaches, digestive disorders, suicidal ideations, or any combination thereof.

In certain embodiments, said anti-sex addiction effect is manifested by a slowing of the progression of one or more symptoms or effects of addiction to sex including, for example, and not by way of limitation, profound depression (sometimes with suicidal thoughts), chronic low self-esteem, shame, self-hatred, hopelessness, despair, helplessness, intense anxiety, HIV infection, genital herpes, HPV, syphilis, gonorrhea, and other sexually transmitted diseases (STDs), or any combination thereof.

In yet another embodiment, this invention is also directed to a method for treating a subject who has been diagnosed as suffering from addiction to substances and behaviors, alcohol, nicotine, prescription drugs, morphine, cocaine or heroin, food, or any combination thereof, and who is in need of therapeutic treatment comprising administering to said subject (a) a therapeutically effective amount of a first composition comprising a balanced PC composition; and (b) a therapeutically effective amount of a second composition comprising one or more cannabinoids, a natural or synthetic derivative thereof, or a salt thereof; wherein said first composition and said second composition are each optionally and independently administered together with a pharmaceutically acceptable carrier or diluent, and wherein said therapeutic treatment is prevention, treatment or amelioration of one or more of the aforementioned symptoms or effects of an addiction to substances and behaviors, alcohol, nicotine, prescription drugs, morphine, cocaine or heroin, food, sex, or any combination thereof.

The invention as described herein provides compositions and methods for preventing, ameliorating and/or treating of diseases and disorders related to impairment of tissue and cell development and activity.

Cannabinoids are medically efficacious for a variety of ailments and diseases. Specifically, cannabinoids are inhibitory to plaque formation, anti-oxidative in nature, impair the formation of cholesteryl esters, and act as vasodilators and smooth muscle relaxants in arterial walls; all of which are beneficial in treating symptoms of seizures and related diseases or disorders.

One of the main variables of membrane lipid composition is the quantitative relationships between sphingomyelin, phosphatidylcholine, and cholesterol, which are the main lipid components of the outer monolayer of mammalian plasma membranes. In most normal cells, there is a gradient of sphingomyelin from the cell boundary to cell center; its highest content is in the plasma membrane, the lowest in the inner mitochondrial membrane and the nuclear membrane. In the mammalian plasma membrane, the two choline-containing lipids, phosphatidylcholine and sphingomyelin constitute more than 50% of the total phospholipid. Sphingomyelin content increases with aging, especially in tissues which have a relatively low phospholipid turnover. It also increases in several diseases, including atherosclerosis and certain types of cancer, which are non-limiting examples of the symptoms and/or effects of addiction to drug substances. For example, a 6-fold change in the sphingomyelin to phosphatidylcholine mole ratio takes place in the aorta and arterial wall during aging of normal humans. The change of this ratio in atherosclerosis is even more striking. In this disease, the sphingomyelin content can be as high as 70-80% of the total phospholipids in advanced aortic lesions.

In general, there is a strong positive correlation between the content of sphingomyelin and cholesterol in membranes. In addition, changes in the content of one are followed by comparable changes in the other. Indeed, it is still not clear how cells maintain the various lipid compositions in their different membranes despite the transfer and exchange of lipids among membranes in vivo. Pathological changes in sphingomyelin content might result from changes in the metabolism of the compound, i.e. increase in its rate of biosynthesis, reduction in its rate of degradation, or change in relative rate in phospholipid transfer in or out of cells. The change taking place in one membrane might remain localized or it may be propagated to other membranes of the cell by transfer of lipid. The relative content of phosphatidylcholine, sphingomyelin, and cholesterol appears to vary in different membrane systems and even within the same membrane under different conditions.

It is believed that oxidized lipids contribute to heart disease both by increasing deposition of calcium on the arterial wall, a major hallmark of atherosclerosis, and by interrupting blood flow, a major contributor to heart attack and sudden death. Oxidized cholesterol (oxysterols) enhances the production of sphingomyelin, which is the elevated phospholipid found in the cellular membranes of occluded coronary arteries. The increase of sphingomyelin content in the cell membrane enhances the interaction between the membrane and ionic calcium ($Ca^{2+}$), thereby increasing the risk of arterial calcification Without intending to be limited to a specific mechanism of action, one possible mechanism of action of the combination therapy of the present invention is through a cascade of one or more biochemical pathways that result in vasodilation and blood thinning, which in turn results in the significant reduction of blood lipids triglyceride, LDL and cholesterol. As a result of the administration of a balanced PC composition that has a blood thinning effect according to the present invention, the transport of one or more cannabinoids through cell membranes and the blood brain barrier is further facilitated. Because of the ease and efficiency of transport of cannabinoids that is caused by use of a balanced PC composition, the effective concentration of cannabinoids can be reduced by as much as about 10 fold to about 100 fold or more without reducing the therapeutic effectiveness of this drug.

The optimization of dosing of cannabinoids achieved with the compositions and methods of the present invention has tremendous clinical advantages in preventing the one or more side effects of use of cannabinoids including, for example, and not by away of limitation those effects such as dysphoria, and anxiety or panic, impairment of memory, reductions in psychomotor and cognitive performance, disordered perception of the passage of time, and euphoria, schizophrenic psychosis, tiredness, dizziness, tachycardia, orthostatic hypotension, dry mouth, reduced lacrimation, muscle relaxation, and increased appetite, potential irreversible cognitive impairments (albeit when used at high concentrations or when being used in children adolescents (particularly before puberty)) or any combination thereof that are known side effects of any cannabinoid-based therapy Thus, without intending to be limited to any specific mechanism of action, it is believed that subjects exhibiting symptoms or deleterious effects of addiction to substances or behaviors or related diseases have a heightened sphingomyelin to phosphatidylcholine relative ratio. Furthermore, the combination therapy of the invention results in a decrease in the relative sphingomyelin to phosphatidylcholine mass ratio. A non-limiting example of the beneficial sphingomyelin to phosphatidylcholine mass ratio achieved with the compositions and methods of the present invention is approximately 1.2-4.2. It is this decrease in the sphingomyelin to phosphatidylcholine ratio that serves to reduce or ameliorate the symptoms of addiction to substances or behaviors or related diseases or disorders such atherosclerosis or related coronary heart disease conditions associated with addiction to substances.

The cannabinoids for use in the compositions and methods of the present invention are isolated endogenous cannabinoids, phytocannabinoids, recombinant cannabinoids, or a combination thereof, can be administered exogenously, or may be administered through a combination of both endogenous and exogenous sources of cannabinoids. In general, administration of cannabinoids with a balanced PC composition increases the bioavailability of cannabinoids.

4. Formulation and Modes of Administration

The terms "treat", "treated", "treating" and "treatment" are to be broadly understood as referring to any response to, or anticipation of, a medical condition in a mammal, particularly a human, and includes but is not limited to: (i) preventing the medical condition from occurring in a subject, which may or may not be predisposed to the condition, but has not yet been diagnosed with the condition and, accordingly, the treatment constitutes prophylactic treatment for the medical condition; (ii) inhibiting the medical condition, i.e., arresting, slowing or delaying the onset, development or progression of the medical condition; or (iii) relieving the medical condition, i.e., causing regression of the medical condition.

The term "therapeutically effective amount" or "therapeutically and/or prophylactically effective amount" as used herein refers to an amount of compound or agent that is sufficient to elicit the required or desired therapeutic and/or prophylactic response, as the particular treatment context may require.

The terms "BodyBio balanced PC", and "balanced PC" are used interchangeably herein.

It will be understood that a therapeutically and/or prophylactically effective amount of a drug for a subject is dependent inter alia on the body weight of the subject as well as other factors known to a person of ordinary skill in the art. A "subject" herein to which a therapeutic agent or composition thereof can be administered includes mammals such as a human subject of either sex and of any age, and also includes any nonhuman animal, particularly a domestic or companion animal, illustratively a cat, dog or a horse as well as laboratory animals such as guinea pigs.

As used herein, an "effective amount" of a composition is an amount sufficient to achieve a desired biological effect, in this case at least one of modulation of activity and/or development of cell populations and/or tissues that are targeted by the combination therapy of the invention. It is understood that the effective dosage will be dependent upon the age, sex, health, and weight of the recipient, kind of concurrent treatment, if any, frequency of treatment, and the nature of the effect desired. The most preferred dosage will be tailored to the individual subject, as is understood and determinable by one of skill in the art, without undue experimentation.

As used herein, a "subject" is any mammal, in particular a primate, preferably a human, that 1) exhibits at least one symptom associated with impairment of tissue development and activity, or 2) and has been diagnosed with an addiction or is at the risk of developing a disease or disorder related to addiction which causes an impairment of tissue development and activity.

In a specific embodiment, the term "pharmaceutically acceptable" means approved by a regulatory agency of the Federal or a state government or listed in the U.S. Pharmacopcia or other generally recognized pharmacopcia for use in animals, and more particularly in humans.

The term "carrier" refers to a diluent, adjuvant, excipient, or vehicle with which the therapeutic is administered. In one embodiment, the therapeutically effective amount of the balanced PC composition of the present invention itself serves as the pharmaceutical carrier for the one or more cannabinoids (for example, and not by way of limitation, the balanced PC composition serves as a liposome, a micelle, or small unilamellar vesicle (SUV) for the entrapment of the therapeutically effective amount of one or more cannabinoids. Such pharmaceutical carriers can be sterile liquids, such as water and oils, including those of petroleum, animal, vegetable or synthetic origin, such as peanut oil, soybean oil, mineral oil, sesame oil and the like. Preferred oil is essential fatty acids, linoleic acid and linolenic acid. Water is a preferred carrier when the pharmaceutical composition is administered intravenously. Saline solutions and aqueous dextrose and glycerol solutions can also be employed as liquid carriers, particularly for injectable solutions.

The active compositions of the invention having tissue modulatory activities as described herein are provided as isolated and substantially purified compounds in pharmaceutically acceptable formulations using formulation methods known to those of ordinary skill in the art. These formulations can be administered by standard routes.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides.

The compositions of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

In general, the combinations may be administered by the transdermal, intraperitoneal, intracranial, intracerebroventricular, intracerebral, intravaginal, intrauterine, oral, rectal, ophthalmic (including intravitreal or intracameral), nasal, topical (including buccal and sublingual), parenteral (including subcutaneous, intraperitoneal, intramuscular, intravenous, intradermal, intracranial, intratracheal, and epidural and nasal) administration. Parenteral administration includes direct or indirect injection into cells, tissues or organs in vivo, ex vivo or in vitro.

In one embodiment, the combination therapy comprising use of a first composition comprising a balanced PC composition and the second composition comprising one or more cannabinoids is administered through one or more different or the same routes of administration in a single or multiple regimen. In one embodiment, first composition comprising a balanced PC composition and the second composition comprising one or more cannabinoids can be administered by a variety of routes and modes of administration, including for example, and not by way of limitation, intravenous routes, transdermal routes, intranasal routes, parenteral routes, oral routes or a combination thereof. In one embodiment, the first composition comprising a balanced PC composition and the second composition comprising one or more cannabinoids is administered once, twice, three, four or more times daily through, IV routes, oral routes, or a combination of both.

Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In one embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachets indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided. The compositions are administered separately or are mixed together prior to administration.

In one embodiment, the first composition, the second composition or both may be incorporated into biodegradable polymers allowing for sustained release of the compound, the polymers being implanted in the vicinity of where drug delivery is desired or implanted so that the composition is slowly released systemically. Osmotic mini-pumps may also be used to provide controlled delivery of the first composition, the second composition or both through cannulae to the site of interest, such as directly into the site of injury. The biodegradable polymers and their use are described, for example, in detail in Brem et al., *J. Neurosurg.* 74: 441-446 (1991), which is hereby incorporated by reference in its entirety.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampoules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

The composition formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers or finely divided solid carriers or both, and then, if necessary, shaping the product.

In another embodiment, the composition of the invention comprises a therapeutically effective amount of a first composition comprising a balanced PC composition formulations and the second composition comprising one or more cannabinoids, in a suitable carrier.

A typical regimen for treatment of symptoms of diseases and disorders related to impaired development and activities of cells and tissues comprises administration of an effective amount of the composition as described above, administered as a single treatment, or repeated as enhancing or booster dosages, over a period up to and including one week to about 48 months or more.

Within other embodiments, the compositions may also be placed in any location such that the compounds or constituents are continuously released. The amount of the composition of the invention which will be effective in the treatment of symptoms of diseases and disorders related to impaired tissue development can be determined by standard clinical techniques. In addition, in vitro assays may optionally be employed to help identify optimal dosage ranges. In particular, the dosage of the compositions of the present invention will depend on the disease state of subject under treatment and other clinical factors such as weight and condition of the human or animal and the route of administration of the compounds or compositions. The precise dose to be employed in the formulation, therefore, should be decided according to the judgment of the health care practitioner and each patient's circumstances. Effective doses may be extrapolated from dose-response curves derived from in vitro or animal model test systems.

Various delivery systems are available and can be used to administer the compositions of the invention, i.e., encapsulation in liposomes, microparticles, microcapsules, recombinant cells capable of expressing the compound, receptor-mediated endocytosis. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (i.e., oral mucosa, rectal and intestinal mucosa, etc.) and may be administered together with other biologically active agents. Administration can be systemic or local.

In addition, it may be desirable to introduce the compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, i.e., by use of an inhaler or nebulizer, and formulation with an aerosolizing agent.

In a specific embodiment, it may be desirable to administer the compositions of the invention locally to the area in need of treatment; this may be achieved by, for example, and not by way of limitation, local infusion during surgery, topical application, i.e., in conjunction with a wound dressing after surgery, by injection, by means of a catheter, by means of a suppository, or by means of an implant, the implant being of a porous, non-porous, or gelatinous material, including membranes, such as sialastic membranes, or fibers. Preferably, when administering a protein such as *cannabis*, care must be taken to use materials to which the protein does not absorb or otherwise interact.

In one embodiment, the compound or composition can be delivered in a controlled release system. In one embodiment, a pump may be used. In another embodiment, polymeric materials can be used. In yet another embodiment, a controlled release system can be placed in proximity of the therapeutic target, i.e., the brain, thus requiring only a fraction of the systemic dose. Other controlled release systems are discussed in the review by Langer, *Science* 249:1527-1533 (1990).

Non-limiting representative examples of various dosage ranges for the first composition comprising a balanced PC composition and the second composition comprising one or more cannabinoids are as follows. In one embodiment, the first composition and/or the second composition is administered at a dosage of about 50 units/kg, 100 units/kg or 150 units/kg at a weekly or biweekly interval. In one embodiment, compositions disclosed herein comprise balanced PC and/or one or more cannabinoids in a total amount of between about 0.1% and about 95% by weight of the combination therapy composition, for example about 0.1%, about 0.2%, about 0.3%, about 0.4%, about 0.5%, about 0.6%, about 0.7%, about 0.8%, about 0.9%, about 1.0%, about 2%, about 3%, about 4%, about 5%, about 6%, about 7%, about 8%, about 9%, about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%, or any numerical integer values there between.

The compositions of the invention can be in a form suitable for oral use, according to any technique suitable for the manufacture of oral pharmaceutical compositions as are within the skill in the art. For example, the phosphatidylcholine composition and the EFA composition can be formulated (either separately or together) into soft capsules, oily suspensions, or emulsions, optionally in admixture with pharmaceutically acceptable excipients.

The compositions of the invention are formulated into liquid, semi-liquid, suspension, or solid compositions, such as aqueous solutions, aqueous or oily suspensions, syrups or elixirs, emulsions, tablets, dispersible powders or granules, hard or soft capsules, optionally in admixture with pharmaceutically acceptable excipients.

5. Adjuvants, Carriers, and Diluents

As would be understood by one of ordinary skill in the art, when a composition of the present invention is provided to an individual, it can further comprise at least one of salts, buffers, adjuvants, or other substances which are desirable for improving the efficacy of the composition. Adjuvants are substances that can be used to specifically augment at least one immune response. Normally, the adjuvant and the composition are mixed prior to presentation to the immune system, or presented separately.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions.

Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

Adjuvants can be generally divided into several groups based upon their composition. These groups include lipid micelles, oil adjuvants, mineral salts (for example, AlK $(SO_4)_2$, AlNa $(SO_4)_2$, AlNH$_4$ $(SO_4)$), silica, kaolin, and certain natural substances, for example, wax D from *Mycobacterium tuberculosis*, substances found in *Corynebacterium parvum*, or *Bordetella pertussis*, Freund's adjuvant (DIFCO), alum adjuvant (Alhydrogel), MF-50 (Chiron) Novasomes™, or micelles, among others.

Suitable excipients for liquid formulation include water or saline, suspending agents such as sodium carboxymethylcellulose, methylcellulose, hydroxypropylmethyl-cellulose, sodium alginate, polyvinylpyrrolidone, gum tragacanth, and gum acacia; dispersing or wetting agents such as lecithin, condensation products of an alkylene oxide with fatty acids (e.g., polyoxethylene stearate), condensation products of ethylene oxide with long chain aliphatic alcohols (e.g., heptadecethyleneoxy-cetanol), condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyoxyethylene sorbitan monooleate).

Suitable excipients for solid formulations include calcium carbonate, sodium carbonate, lactose, calcium phosphate, or sodium phosphate; granulating and disintegrating agents such as maize starch, or alginic acid; binding agents such as starch, gelatin, or acacia; and lubricating agents such as magnesium stearate, stearic acids, or talc, and inert solid diluents such as calcium carbonate, calcium phosphate, or kaolin.

Other suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides.

The amount of the composition of the invention which will be effective in the treatment, inhibition and prevention of a disease or disorder associated with tissue or cell impairment can be determined by standard clinical techniques. In addition, in vitro assays may optionally be employed to help identify optimal dosage ranges.

In particular, the dosage of the composition of the present invention will depend on the disease state or condition being treated and other clinical factors such as weight and condition of the human or animal and the route of administration of the compound. The precise dose to be employed in the formulation, therefore, should be decided according to the judgment of the practitioner and each patient's circumstances. Effective doses may be extrapolated from dose-response curves derived from in vitro or animal model test systems.

For treating humans or animals, between approximately 0.5 to 500 mg/kilogram, is a typical broad range for administering the pharmaceutical composition of the invention. The methods of the present invention contemplate single as well as multiple administrations, given either simultaneously or over an extended period of time. It is to be understood that the present invention has application for both human and veterinary use.

Preferred unit dosage formulations are those containing a daily dose or unit, daily sub-dose, as herein above recited, or an appropriate fraction thereof, of the administered ingredient. It should be understood that in addition to the ingredients, particularly mentioned above, the formulations of the present invention may include other agents conventional in the art having regard to the type of formulation in question.

6. Test Kits

The invention also provides a combination therapy pack or kit comprising one or more containers filled with one or more compositions comprising a balanced PC composition and one or more cannabinoid compositions of the combined therapy of the invention. The kits are provided for the treatment of the symptoms of disease and disorders related to impaired development and activities of cells and tissues. The kit comprises instructions for treating addiction to substances or a related disease or disorder as described supra in a subject and one or more of the following components: 1) a first composition comprising a balanced PC composition; 2) a second composition comprising one or more cannabinoids; and 3) optionally associated with such container(s) can be a notice in the form prescribed by a governmental agency regulating the manufacture, use or sale of pharmaceuticals or biological products, which notice reflects approval by the agency of manufacture, use or sale for human administration.

If a particular component is not included in the kit, the kit can optionally comprise information on where to obtain the missing component, for example an order form or uniform resource locator for the internet specifying a website where the component can be obtained. The instructions provided with the kit describe the practice of the methods of the invention as described above, and the route of administration and effective concentration and the dosing regimen for each of the compositions provided therein.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims. The contents of all references, patents and published patent applications cited throughout this application are expressly incorporated herein by reference.

EXAMPLES

Example 1

Production of Bodybio Balanced PC

BodyBio Balanced PC contains is a phosphatidyl-choline, phosphatidyl-ethanolamine, phosphatidyl-inositol, phosphatidic acid, and mixed glycerol phospholipids formulated as a water-soluble supplement extracted from soy lecithin (lecithin is oil based and is not water-soluble).

The fatty acids and phospholipid concentrations in the intermediate phosphatidylcholine compound are presented below. These percentage values provided below represent a non-limiting example of fatty acid content and of the various phospholipids found in the composition.

Fatty Acid Content:
C16.0 16.1%
C16.1 0.1%
C18.0 4.1%
C18.1 10.0%
C18.2 55.30% (omega 6)
C18.3 14.0% (omega 3)
C22.0 0.4%

Phosphotidylcholine (PC): about 29%
Phosphotidylethanolamine (PE): about 16%
Phosphatidyl inositol (PI): about 9%
Phosphatidic Acid (PA): about 4%
Phosphatidylglycerol (PG): about 1%
Total PLs: about 61%

Example 2

Production of Bodybio Balanced PC Cannabinoid Combination Composition

Prepare BodyBio Balanced PC as in Example 1, Supra.

Prepare a 1:1 mix of tetrahydrocannabinol (THC), cannabidiol (CBD).

Dissolve 1:1 mix of THC and CBD in pure deionized RO water.

Add ⅓ BodyBio balanced PC into the 1:1 mix of THC and CBD dissolved in pure deionized RO water and agitate violently for 5-10 seconds to produce a gelatinous state.

The BodyBio balanced PC composition—cannabinoid composition was then treated with a Sonic mixer (e.g., with a Branson 250 Sonic mixer) to generate a liposome size of approximately 5-10 microns.

In other embodiments, the liposomes are small unilamellar vesicles (SUVs) having sizes predominantly between 0.02 and 0.08 microns in size.

Example 3

Treatment of Patients with Addiction with Combination Therapy

Case History Resistant Substance Abuse
Patient Background: A 41-year old female presents with treatment resistant substance abuse involving alcohol, prescription pain meds and tobacco for the past 20 years. Height: 5'6", Weight: 150 lbs
Presenting Symptoms include depression, anxiety, panic, headaches, mood swings, rage behavior fatigue, PMS, constipation
Family history of alcoholism, cancer, diabetes
Current Medications: no prescribed meds
Clinical Profile:
  i) Test results prior to oral and intravenous PC
    Electrolyte imbalance—low potassium
    Hepatic stress—elevated liver enzymes (GGT, LDH), blood urea nitrogen
    Hyperglycemia—elevated glucose and hemoglobin A1c
  ii) Patient was treated over 7 days in a rehab center with oral and IV PC
Clinical Course:
Patient had 3 failed attempts at a detox rehab center. Although she responded positively to IV amino acids and oral vitamins/minerals in the first and second weeklong detox sessions 3 months apart, within weeks of leaving the center she would relapse. Her physician suggested intravenous and oral phosphatidylcholine which held the intense cravings in check for a longer period of time in regard to pain medication. Without continued therapy, the patient's craving for tobacco and alcohol resurfaced.

The introduction of one or more cannabinoids listed supra with balanced BodyBio PC would be supportive in the control of the use of recreational drugs, pain meds, tobacco and alcohol.

The inclusion of one or more cannabinoids in combination with BodyBio's balanced Phosphatidylcholine may serve to function similarly to the endocannabinoids and synergystically bring about the blockade of one or more moieties in the cell membrane, including, for example, the CB1 receptor. The blockade of the CB1 receptor in turn modulates the inflammatory state in atheromata, which in turn in combination with BodyBio's balanced Phosphatidylcholine serves to reduce the sphingomyelin to PC ratio, and as a result, the DMAs are lowered by competitive inhibition.

The lowering of the DMA ratio results in a lowering of the plasminogens in the cell membrane which directly correlates with the lowered concentration of sphingomylenin and calcium in the cell membrane. This lowered concentration of sphingomylenin and calcium leads to a normalizing of the lipid bilayer membrane leaflets and maximizing the integrity of the membrane which resulted in patient's sphingomyelin/PC ratios approaching more normalized ratios.

All references, including publications, patent applications, and patents, cited herein are hereby incorporated by reference to the same extent as if each reference were individually and specifically indicated to be incorporated by reference and were set forth in its entirety herein.

The use of the terms "a," "an" and "the" and similar references in the context of this disclosure (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., such as, preferred, preferably) provided herein, is intended merely to further illustrate the content of the disclosure and does not pose a limitation on the scope of the claims. No language in the specification should be construed as indicating any non-claimed element as essential to the practice of the present disclosure.

The individual numerical values are stated as approximations as though the values were preceded by the word "about" or "approximately." Similarly, the numerical values in the various ranges specified in this application, unless expressly indicated otherwise, are stated as approximations as though the minimum and maximum values within the stated ranges were both preceded by the word "about" or "approximately." In this manner, variations above and below the stated ranges can be used to achieve substantially the same results as values within the ranges. As used herein, the terms "about" and "approximately" when referring to a numerical value shall have their plain and ordinary meanings to a person of ordinary skill in the art to which the disclosed subject matter is most closely related or the art relevant to the range or element at issue. The amount of broadening from the strict numerical boundary depends upon many factors. For example, some of the factors which may be considered include the criticality of the element and/or the effect a given amount of variation will have on the performance of the claimed subject matter, as well as other considerations known to those of skill in the art. As used herein, the use of differing amounts of significant digits for different numerical values is not meant to limit how the use of the words "about" or "approximately" will serve to broaden a particular numerical value or range. Thus, as a general matter, "about" or "approximately" broaden the numerical value. Also, the disclosure of ranges is intended as a continuous range including every value between the minimum and maximum values plus the broadening of the range afforded by the use of the term "about" or "approximately."

Thus, recitation of ranges of values herein are merely intended to serve as a shorthand method of referring individually to each separate value falling within the range, unless otherwise indicated herein, and each separate value is incorporated into the specification as if it were individually recited herein.

It is to be understood that any ranges, ratios and ranges of ratios that can be formed by, or derived from, any of the data disclosed herein represent further embodiments of the present disclosure and are included as part of the disclosure as though they were explicitly set forth. This includes ranges that can be formed that do or do not include a finite upper and/or lower boundary. Accordingly, a person of ordinary skill in the art most closely related to a particular range, ratio or range of ratios will appreciate that such values are unambiguously derivable from the data presented herein.

Alternative embodiments of the claimed disclosure are described herein, including the best mode known to the inventors for practicing the claimed invention. Of these, variations of the disclosed embodiments will become apparent to those of ordinary skill in the art upon reading the foregoing disclosure. The inventors expect skilled artisans to employ such variations as appropriate (e.g., altering or combining features or embodiments), and the inventors intend for the invention to be practiced otherwise than as specifically described herein.

Accordingly, this invention includes all modifications and equivalents of the subject matter recited in the claims appended hereto as permitted by applicable law. Moreover, any combination of the above described elements in all possible variations thereof is encompassed by the invention unless otherwise indicated herein or otherwise clearly contradicted by context.

What is claimed is:

1. A method for treating, or ameliorating one or more symptoms of a prescription drug addiction in a subject comprising administering to said subject (a) a therapeutically effective amount of a first composition consisting of a balanced phosphatidylcholine PC composition; and (b) a therapeutically effective amount of a second composition consisting of one or more cannabinoids, the balanced PC composition is a water-soluble supplement extracted from soy lecithin consisting of phospholipids and essential fatty acids; the phospholipids consisting of phosphatidylcholine, phosphatidylethanolamine, and phosphatidylinositol, and other phospholipids; the essential fatty acids consisting of omega 6 and omega 3 fatty acids in a weight ratio of 4:1 respectively.

2. The method of claim 1, wherein the balanced phosphatidylcholine (PC) composition and the cannabinoids are administered at different time intervals.

3. The method of claim 1, wherein the balanced PC composition, the cannabinoids, or both are administered parenterally, transdermally, intranasally, or intravenously.

4. The method of claim 1, wherein the balanced PC composition and the cannabinoids are administered successively, contemporaneously, or both, at different time intervals.

5. The method of claim 1, wherein the balanced PC composition and the cannabinoids are administered in a time-released manner.

6. The method of claim 1, wherein the balanced PC composition and the cannabinoids are formulated in one or more solution formulations.

7. The method of claim 1, wherein the cannabinoids comprise natural and synthetic cannabinoids.

8. The method of claim 7, wherein the natural cannabinoids are selected from Cannabidiol (CBD), Cannabinol (CBN), Cannabigerol (CBG); Cannabichromene (CBC); Cannabicyclol (CBL); Cannabivarin (CBV); Tetrahydrocannabivarin (THCV); Cannabidivarin (CBDV); Cannabichromevarin (CBCV); Cannabigerovarin (CBGV); Cannabigerol Monomethyl Ether (CBGM); and Tetrahydrocannabinol (THC), or a combination thereof.

9. The method of claim 7, wherein the natural cannabinoids are selected from phytocannabinoids derived from *Echinacea purpurea, Echinacea angustifolia, Echinacea pallida, Acmella oleracea, Helichrysum umbraculigerum*, and *Radula marginata*, or a combination thereof.

10. The method of claim 7, wherein the synthetic cannabinoid variants are selected from Dronabinol (Marinol) (Δ9-tetrahydrocannabinol (THC)), Nabilone (Cesamet), Sativex, and Rimonabant (SR141716), or a combination thereof.

* * * * *